United States Patent [19]

Krajicek

[11] Patent Number: 5,522,840
[45] Date of Patent: Jun. 4, 1996

[54] DEVICE FOR THE NON-SURGICAL SEAL OF THE INTERSTICE IN THE WALL OF A VESSEL

[76] Inventor: Milan Krajicek, 5. Kvetna 19, 140 00 Praha 4, Czechoslovakia

[21] Appl. No.: 151,712

[22] Filed: Nov. 12, 1993

[30] Foreign Application Priority Data

Nov. 23, 1992 [CS] Czechoslovakia ............... 3455-92

[51] Int. Cl.⁶ ........................................... A61B 17/00
[52] U.S. Cl. .................... 606/213; 623/12; 604/285; 604/286; 604/288; 604/280
[58] Field of Search ................... 606/213, 215, 606/151, 153, 154, 155; 623/11, 12; 128/887; 604/285–288, 280, 265, 160, 161

[56] References Cited

U.S. PATENT DOCUMENTS

| | | | |
|---|---|---|---|
| 2,127,903 | 8/1938 | Bowen | 606/154 |
| 4,615,705 | 10/1986 | Scales et al. | 623/11 |
| 4,778,467 | 10/1988 | Stensaas et al. | 623/12 |
| 4,841,962 | 6/1989 | Berg et al. | 602/50 |
| 4,997,439 | 3/1991 | Chen | 606/213 |
| 5,192,300 | 3/1993 | Fowler | 606/213 |
| 5,254,105 | 10/1993 | Haaga | 604/265 |
| 5,290,310 | 3/1994 | Makower et al. | 606/213 |
| 5,334,216 | 8/1994 | Vidal et al. | 606/151 |

OTHER PUBLICATIONS

Sjef M. P. G. Ernst, MD et al., "Immediate Sealing of Arterial Puncture Sites After Cardiac Catheterization and Coronary Angioplasty Using A Biodegradable Collagen Plug: Results of an International Registry", *J AM Coll Cardiol*, 1993;21–4, pp. 851–855.

Brochure on "Datascope Introduces VasoSeal™" (date unknown).

Brochure entitled, "The Hemostatic Puncture Closure Device", of Kensey Nash Corporation (date unknown).

"Kinsey Nash/Quinton Arterial Puncture Hemostosis Device", Industry & Washington Memos (M–D–D–I Reports), Nov. 18, 1991.

*Primary Examiner*—Stephen C. Pellegrino
*Assistant Examiner*—Jeffrey A. Schmidt
*Attorney, Agent, or Firm*—Panitch Schwarze Jacobs & Nadel

[57] ABSTRACT

A device for non-surgical sealing of the interstice in the wall of a vessel is provided. The device includes a tubular, resorbable collagen plug 4 having longitudinal cut 8 in the form of a V. The device can further include applicator 5. The opening of cut 8 of plug 4 is located on the peripheral portion of plug 4. The internal diameter of plug 4 corresponds to the external diameter of catheter 3 which is introduced into vessel 1. The external diameter of plug 4 corresponds to the external diameter of applicator 5. Plug 4 includes inner and outer layers of resorbable collagen which have differing swelling rates. Applicator 5 includes longitudinal cut 10 in the form of a V. The opening of cut 10 is located on the peripheral side of applicator 5 relative to vessel 1.

13 Claims, 3 Drawing Sheets

DEVICE FOR THE NON-SURGICAL SEAL OF THE INTERSTICE IN THE WALL OF A VESSEL

FIELD OF THE INVENTION

The invention provides a device for the non-surgical sealing of the interstices in the wall of a vessel created intentionally by the introduction of a catheter for diagnostic or therapeutic reasons.

BACKGROUND OF THE INVENTION

In the field of diagnosis and therapy of vascular, cardiac, oncological and other diseases, non-surgical methods are used more and more. The principal uses in the scope of these methods are those which use a catheter introduced intraluminally into vessels, particularly arteries. In accordance with the reasons for the introduction of catheters, catheters of different external diameters are used. The unit generally used to identify the diameter is called "French". One French is about 0.3 mm. The most commonly used catheters are in the range of 6 to 8 Frenches. In recent times, a quite short external catheter called "sheet" has also been used more and more. A sheet is basically a synthetic tube 10 to 15 cm long, and its internal diameter is equal to the external diameter of the catheter used. The wall of a "sheet" is very thin, about 0.1 mm. The procedure is such that after the puncture of an artery, or possibly another vessel, by a thin needle a wire guide is introduced through this thin needle, and the needle is then removed. Using the wire-guide as the leader, a catheter, or possibly a catheter with a sheet, is introduced into a vessel.

After the diagnostic or therapeutic procedure is finished, the catheter is removed, but an interstice of proportionate dimension remains in the wall of the vessel. In point of fact, in 90% of cases when an artery is punctured, significant bleeding through the interstice occurs due to arterial pressure. The spontaneous sealing of the interstice by a thrombus can generally be achieved by manually applying pressure to the vessel transcutaneously in the proper place for about 20 minutes. During the following 24 hours, the patient stays in a horizontal position and a bag filled with sand weighing about 2.0 kg is placed transcutaneously on the location of the puncture, mostly in the groin. This approach has, of course, quite a few disadvantages. At first, the patient has to lie in a horizontal position. This means that hospitalization is necessary for at least for one day. On the one hand, this increases demand for bed capacity, and on the other hand increases expense. Further, in some cases, even when using the above-described procedure, one of two complications can occur. One is that bleeding is not completely stopped or that bleeding resumes after some time. In this case, surgical intervention with direct suture of the interstice in the wall of the vessel is necessary. Less often, but not exceptionally, the manual compression is too effective and a thrombus develops to occlude not only the interstice in the wall of the vessel but also the lumen of the vessel with all associated consequences. In this case also surgical intervention is necessary. In both cases hospitalization is prolonged and expenses increase.

From the literature, two attempts for solution of this problem are presently known. Both reportedly are undergoing clinical examination. The first is known under the name "VASOSEAL". In accordance with a published description thereof, before puncture of an artery, the distance between the skin and the vessel is measured. When the procedure is finished and the catheter removed, then in accordance with the data on the measuring device, a special applicator is introduced into the wall of the vessel. By this applicator, collagen in an amorphous form (as illustrated) is applied to the interstice in the wall. Using the applicator, the collagen is compressed against the wall for five minutes to seal the interstice. The other approach is known under the name "Hemostatic Puncture Closing Device". According to the literature, the device comprises a polymer anchor, collagen plug and resorbable fiber. After removal of the catheter by a method which is not entirely clear from the description, the anchor with the fiber is introduced into the wall of the vessel so that the fiber fixes the collagen plug over the interstice.

The basic disadvantage of both approaches is that they can be employed only after the catheter or the sheet is removed. Bleeding appears immediately, and even in the case of very fast application, the development of certain hematoma cannot be prevented. This is in addition to the discomfort of working in the bleeding area. Another disadvantage is that the treated vessel cannot be used for another puncture for at least one month. The second approach described above is also complicated, and for proper execution, some special training is necessary, particularly for personnel without surgical training. Also, both devices are expensive, and particularly in countries with inferior levels of medical care, the cost for a device can be higher than the cost for one-day of hospitalization.

SUMMARY OF THE INVENTION

The aforementioned disadvantages are eliminated by the device in accordance with the invention, which device is simple, fast and economical, and is applied before the catheter or the sheet is removed. Its principle is that as a guide, it uses the catheter or the sheet when it is still in the vessel so that no bleeding occurs after the catheter is removed. In accordance with the invention, the principle resides in the fact that the device is represented by a collagen plug in the form of a tube with a longitudinal cut in the form of a narrow V. The opening of the cut is on the peripheral side of the plug relative to the position of the vessel. The internal diameter of the resorbable collagen plug is substantially equal to the external diameter of the catheter or sheet used. For introduction of the plug, a special applicator is provided whose form and wall thickness are nearly equal to the form and the wall thickness of the resorbable collagen plug. The applicator is also longitudinally cut in the form of a narrow V, which cut is on the peripheral side of the applicator relative to the portion of the vessel.

Other advantageous forms of the device are clear from the patent claims.

BRIEF DESCRIPTION OF THE DRAWINGS

The invention is further explained in detail with examples in connection with the drawings.

DETAILED DESCRIPTION OF THE INVENTION

Figure 1:
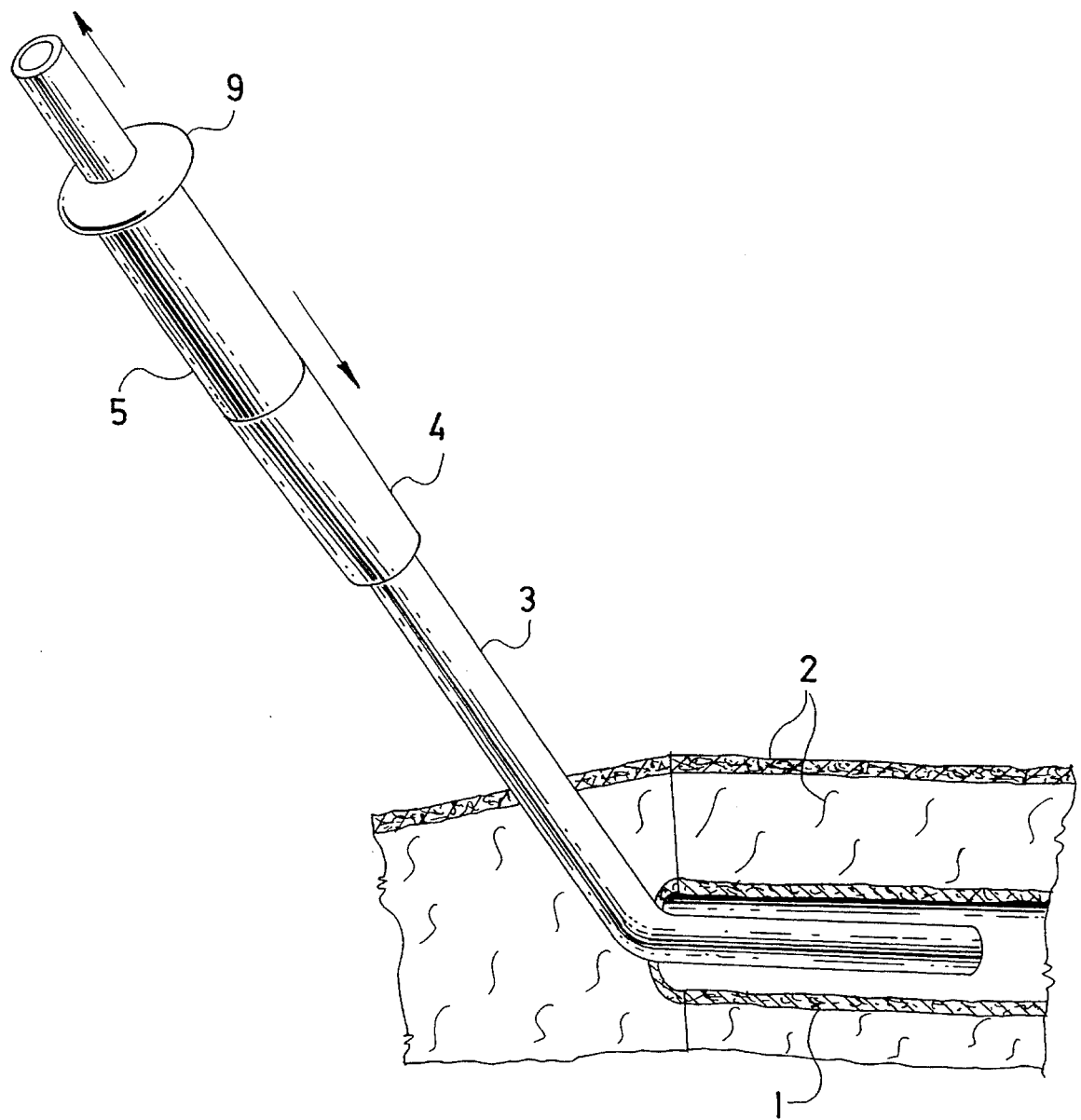
FIG. 1 schematically illustrates the use of the device employing an introduced catheter as the guide.
Figure 2:
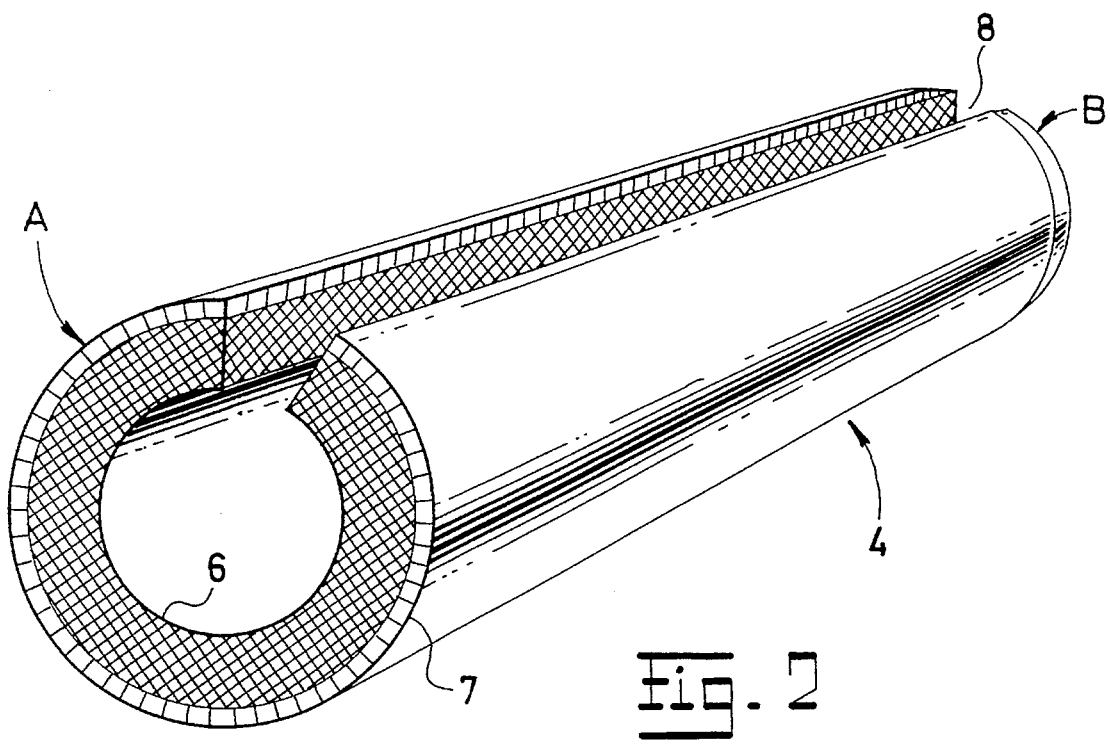
FIG. 2 illustrates a double-layer collagen plug.
Figure 3:
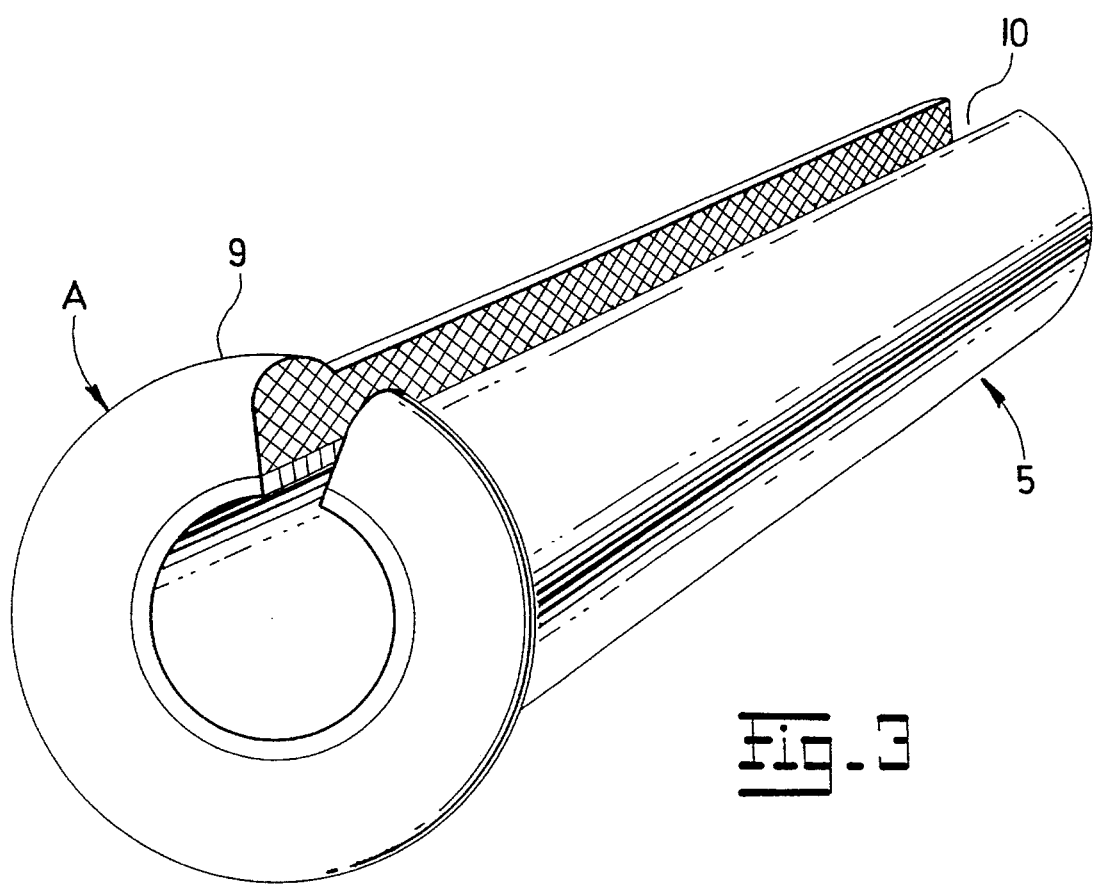
FIG. 3 schematically illustrates a basic type of solid applicator manufactured from an inert material.

The device is formed from two parts. The first part is a resorbable collagen plug 4 which is made by a known method from two types of compressed collagen sponges. Internal layer 6 is made from less tanned, and therefore more rapidly expanding collagen sponge and represents about 80% of the total thickness of the wall of the device. External layer 7 is made from more tanned and therefore less rapidly swelling sponge. It represents about 20% of the total thickness of the wall of the device. Both layers are firmly compressed together. Resorbable double-layer collagen plug 4 is hollow inside throughout the entire length thereof, with an internal diameter substantially equal to the external diameter of catheter 3 or sheet 16 on which it is to be used. Resorbable collagen plug 4 thereby essentially forms a tube. On one side resorbable collagen plug 4 has a longitudinal cut 8 in the form of a narrow V throughout its whole length. When the opening of the V is on the peripheral side A of the device relative to the position of vessel 1, its dimension does not exceed one quarter of the circumference of peripheral side A. Central side B of the device relative to the position of vessel 1 is slightly pointed for easier insertion of resorbable collagen plug 4 into the channel from skin 2 to vessel 1 created by introduction of catheter 3. Before insertion, resorbable collagen plug 4 is stiff, particularly its external layer 7. Swelling occurs only after resorbable collagen plug 4 contacts a fluid, i.e., blood and tissue fluid, so that internal layer 6 first swells up in about thirty seconds. Later, up to about two minutes, external layer 7 also swells. This guarantees ease of introduction of resorbable collagen plug 4 directly into the wall of vessel 1, because external layer 7 retains its structural stability for a sufficient time period.

A second part of the device is applicator 5, manufactured from rigid, biologically inert and sterilizable material, for example from synthetic material, stainless-steel, etc., and which basically has the identical form and wall thickness as the double-layer resorbable collagen plug 4. Applicator 5 also has a longitudinal cut 10 in the form of a narrow V, and the opening of the V is on the peripheral side A of the device relative to the position of vessel 1. The dimension of cut 10 does not exceed one quarter of the circumference of peripheral side A. On peripheral side A the tube of applicator 5 on part of its circumference is also externally broadened in the form of a surface 9 as a thumb support for pressing of resorbable collagen plug 4 on catheter 3 into the wall of vessel 1.

For each external diameter of catheter 3 or sheet 16, an individual internal diameter of the double-layer resorbable collagen plug 4 is assigned, as well as the internal diameter of applicator 5. Both parts are packed in a safe double-package for delivery after having been sterilized by beta or gamma irradiation.

Figure 4:
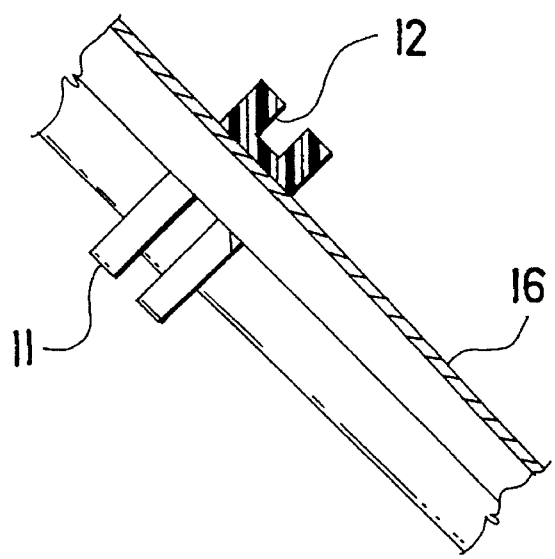
FIG. 4 schematically illustrates the applicator adapted for the use with a sheet. The applicator is composed from two parts.
Figure 5:
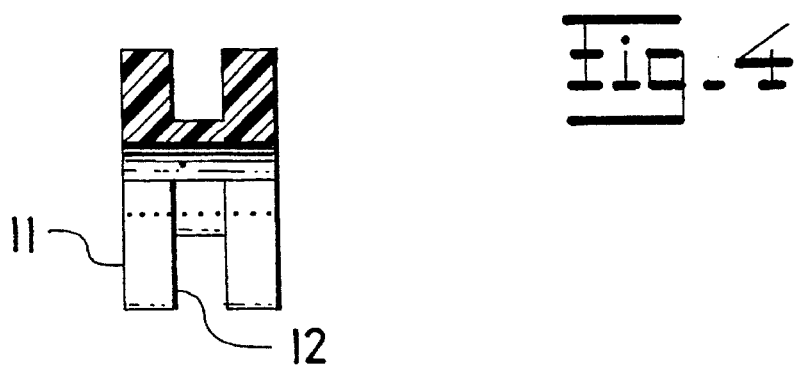
FIG. 5 illustrates the detail of a tubular ring.
Figure 6:
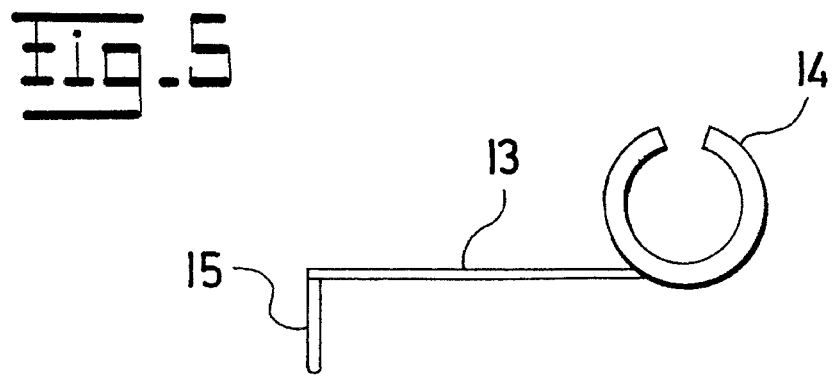
FIG. 6 illustrates the detail of a bar for application on the ring of the applicator in accordance with FIG. 4.

Following (in FIGS. 4–6) is described a modification of the device for particular use with sheet 16. This device is substantially shorter and is not connected with a pump or other equipment. It is therefore possible to place on its external end, even before use, a tubular ring 11 of the applicator. In view of the fact that the whole length of the applicator would complicate manipulation of the sheet, this device consists of two parts. Tubular ring 11, applied on sheet 16, is provided on its whole circumference with a split-groove 12. Before actual use, the central end of the rod 13, which has a catching port in the form of a gapped ring-like end 14 of equal dimensions, is pressed into the split-groove 12. In this way, it is possible to apply sufficient pressure on tubular ring 11 on sheet 16 using broadened part 15 on the peripheral end of rod 13 for support of a thumb, and after use, to also remove it from the tissue.

Following is described manipulation with the device. Catheter 3 is transcutaneously introduced by puncture through skin 2 and subcutaneous tissue into vessel 1. Just before removal of catheter 3, collagen plug 4 is placed on catheter 3 peripherally from skin 2 using its longitudinal cut 8, beginning on peripheral side A where the V form opening of the longitudinal cut 8 is located. When resorbable collagen plug 4 is placed onto catheter 3, a similar procedure is employed to place rigid, tubular applicator 5 onto catheter 3 externally from the plug 4. By applying pressure to applicator 5 while on catheter 3, double-layer resorbable collagen plug 4 is pressed into the wall of the vessel. Under continuous pressure on double-layer resorbable collagen plug 4 by applicator 5, catheter 3 is removed from the vessel. By way of applicator 5, double-layer resorbable plug 4 is pressed on the wall of vessel 1 for about five minutes. During this time, both layers 6 and 7 of the compressed collagen sponge swell, and in the manner of the standard hemostatic sponge substantially accelerate and qualitatively improve development of a resistant thrombus.

Following are examples of the formation of the individual layers:

EXAMPLE 1

From bovine collagen matter a sponge is manufactured by a known method. Into the sponge intended for internal layer 6, no tanning agent is added. Into the sponge intended for external layer 7 is added, even before lyophilization, about 0.2% of glutaraldehyde or methylglyoxal on a dry basis. After the sponge is created, the sponge which is intended for internal layer 6 is wrapped onto a rigid, stainless-steel mandrel to an adequate thickness and compressed to 20% of its original thickness. After stabilization of this form, it is wrapped in an adequate thickness of tanned collagen sponge and again compressed to 10–20% of its original thickness. When the resulting form is stabilized and both layers are mutually fixed, the total thickness of the wall in the dry state does not exceed 2 mm. The external diameter of the stainless-steel mandrel on which compression is performed is equal to the external diameter of catheter 3 or sheet 16 for which the double-layer collagen plug is developed. While on the mandrel, a special instrument is employed to make longitudinal cut 8, and the double-layer resorbable collagen plug is removed from the mandrel. The advantageous length of the whole double-layer resorbable collagen plug is 2 cm, but for use with obese patients, it is also possible to manufacture substantially longer double-layer resorbable collagen plugs. Together with rigid applicator 5 of corresponding dimensions, both parts are put into a double-wall safe package and sterilized by irradiation.

EXAMPLE 2

From bovine collagen matter a sponge is created by known procedures. Before lyophilization in a dish where the lyophilization is to be executed, stainless-steel mandrels are placed in the middle of a collagen layer, which is advantageously 10 mm thick. The stainless-steel mandrels have an external diameter of the intended internal diameter of the double-layer resorbable collagen plug 4, and lyophilization is then executed. Thereafter, the sponge is cut between the mandrels so that the thickness of the collagen sponge around the mandrel is practically uniform. The sponge is then compressed onto the mandrel to 10–20% of its original thickness, and the resulting form is placed with the mandrel into the middle of a tanned collagen layer, advantageously not exceeding 6 mm in thickness. Lyophilization is then executed, and after completion, the sponge is again cut between the mandrels so that the thickness of the sponge around the mandrel is nearly uniform. Also, this layer is compressed to 10–20% of its original thickness. After the form is stabilized, a special instrument is employed to execute longitudinal cut 8 directly on the mandrel, and thereafter the double-layer resorbable collagen plug is removed.

EXAMPLE 3

Into collagen matter of bovine origin, prior to lyophilization, a homogenized thromboplastically active agent is placed, for example human thrombin, in a dosage of 1000 μ/l g dry collagen or 1% chitosan/dry collagen.

EXAMPLE 4

Into collagen matter, prior to lyophilization, an antimicrobiologically active agent is homogenized, for example Neomycin at a dosage of 0.5 g/l g of dry collagen.

EXAMPLE 5

The method is the same as in Examples 1–4, but collagen harvested from bovine tendons is used as the primary material.

EXAMPLE 6

Because the main reason for external layer 7 is to retain structural stability of double-layer resorbable collagen plug 4 for the time necessary for introduction of double-layer resorbable collagen plug 4 into the wall of vessel 1, internal layer 6 is created from collagen sponge by compression onto a rigid mandrel up to 90% of the total thickness of the wall. External layer 7 is formed by repeated application of the tanned amorphous collagen material or by wrapping with film made from tanned collagen material. After this, the whole structure must be allowed to dry completely.

Of course, it is also possible to create just a one-layer collagen plug, but the characteristics of the double-layer plug are superior.

I claim:

1. A device for non-surgical sealing of an interstice in a wall of a vessel (1) created by introduction of a tubular medical device (3) into vessel (1) comprising, a resorbable sponge plug (4) in the form of a tube having a longitudinal cut (8) in the form of a V, the resorbable plug having an internal diameter substantially equal to an external diameter of the tubular medical device (3), the resorbable plug (4) comprising an inner layer of a first biologically resorbable sponge material and an outer layer of a second biologically resorbable sponge material, each of the first and second sponge materials comprising fibrillar protein, and the inner layer and the outer layer both being compressed and having different swelling capacities and swelling rates.

2. The device of claim 1, wherein the resorbable plug (4) has a conical external shape having a wide base on one end and a narrow top on another end.

3. The device of claim 1 further comprising an applicator for pressing said plug into a vessel (1), said applicator (5) having a longitudinal cut in the form of a V on one side (A).

4. The device of claim 3, wherein the applicator (5) has on one end a broadened area (9) for support of a human thumb.

5. The device of claim 3 wherein the applicator (5) is formed from a biologically inert, rigid, sterilizable material.

6. The device of claim 5 wherein the biologically inert material is selected from the group consisting of stainless-steel and TEFLON.

7. The device of claim 1, wherein the resorbable plug (4) has a pointed end portion.

8. The device of claim 1 wherein the fibrillar protein material comprises collagen.

9. The device of claim 1 wherein the fibrillar protein contains a thromboplastically effective agent selected from the group consisting of thrombin, chitosan, and fibrinogen.

10. The device of claim 1 wherein the fibrillar protein of the resorbable collagen plug (4) includes an anti-microbiologically active agent selected from the group consisting of neomycin and rifamycin.

11. The device of the claim 1 wherein the fibrillar protein includes an X-ray contrast agent.

12. The device according to claim 1, wherein the tubular medical device (3) is a catheter.

13. A device for non-surgical sealing of an interstice in a wall of a blood vessel created by introduction of a catheter comprising, a resorbable collagen sponge plug comprising at least one layer of compressed collagen material in the form of a tube having a longitudinal cut in the form of a V, the resorbable plug having an internal diameter substantially equal to an external diameter of the catheter, and an applicator for pressing said plug into the vessel, said applicator having a longitudinal cut in the form of a V on one side, wherein the applicator comprises a tubular ring having a split-groove and a rod provided with a split-ring end for engaging the split-groove, the rod including a portion distal from the split-ring end for support of a human thumb.

\* \* \* \* \*